(12) United States Patent
Soon et al.

(10) Patent No.: US 8,218,234 B2
(45) Date of Patent: Jul. 10, 2012

(54) ILLUMINATION DEVICE FOR A MICROSCOPE

(75) Inventors: Haw Chong Soon, Widnau (CH); Manfred Kuster, Widnau (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 499 days.

(21) Appl. No.: 12/389,261

(22) Filed: Feb. 19, 2009

(65) Prior Publication Data

US 2009/0213457 A1 Aug. 27, 2009

(30) Foreign Application Priority Data

Feb. 28, 2008 (DE) .......................... 10 2008 011 527

(51) Int. Cl.
*G02B 21/06* (2006.01)

(52) U.S. Cl. ...................... 359/388; 359/385; 359/368

(58) Field of Classification Search ........... 359/368–390
See application file for complete search history.

(56) References Cited

U.S. PATENT DOCUMENTS

| | | | |
|---|---|---|---|
| 5,627,613 A * | 5/1997 | Kaneko | 351/221 |
| 5,838,491 A | 11/1998 | Gartner et al. | |
| 6,392,797 B2 * | 5/2002 | Strahle | 359/389 |
| 6,483,642 B1 * | 11/2002 | Deverin | 359/389 |
| 6,624,932 B2 * | 9/2003 | Koetke | 359/389 |
| 6,816,304 B2 * | 11/2004 | Nakamura et al. | 359/388 |

FOREIGN PATENT DOCUMENTS

| | | |
|---|---|---|
| DE | 197 28 035 | 3/2007 |
| EP | 1 326 116 | 9/2007 |

* cited by examiner

*Primary Examiner* — Thong Nguyen

(74) *Attorney, Agent, or Firm* — Nelson Mullins Riley & Scarborough, LLP

(57) ABSTRACT

An illumination device for a microscope has a variable working distance (d, d'), at which an object is illuminated obliquely from two different directions. Light from a light source is split into at least two illumination beam paths. In order to adapt to the different working distances, the light is subjected to an angle change before splitting or, if after splitting, then respectively by the same amount in both beam paths. A deviating element with at least two reflective surfaces is arranged in one of the illumination beam paths to induce a change in an angle at which one of the illumination beam paths strikes the object, in the same sense as another illumination beam path. The reflective surfaces may be arranged so that the illumination beam paths strike essentially the same region of the optical axis even with different working distances.

33 Claims, 5 Drawing Sheets

ILLUMINATION DEVICE FOR A MICROSCOPE

The invention concerns the field of light microscopy and relates to an illumination device for a microscope with a variable working distance, in which the illumination light is guided to the object (oblique illumination) obliquely with respect to the objective. The illumination device is suitable for an operation microscope.

BACKGROUND OF THE INVENTION

In microscopes with direct illumination, the illumination light is guided either through the objective, and therefore parallel or at a small angle with respect to the optical axis of the observation optics, or past the objective, and therefore at a larger angle with respect to the optical axis. The latter arrangement is known as oblique illumination. Oblique illumination has the advantage that the illumination light is not reflected back by the object into the observer's eye. In this way, for example in operation microscopes, dazzling of the operator is avoided. Another advantage is that such illumination devices can be produced with a smaller installation height, since it is possible to obviate elements which inject the illumination light into the objective near the axis of the observation optics and correspondingly add a certain height to the device along that axis.

Oblique illumination, however, can lead to shadowing of the object to be illuminated if objects or structure are present above the object plane and slightly offset from the observation optics' axis. This may occur, for example, in certain operation techniques in which a more deeply lying tissue section is accessed through a narrow opening.

In order to resolve this problem, oblique illumination has been proposed with two illumination beam paths on opposite sides of the observation optics' axis, thereby increasing the likelihood that at least one of the beams will illuminate the object without shadow. The two beam paths extend at an angle relative to one another and with respect to the optical axis of the observation optics. EP-A 1 326 116 discloses a microscope with an illumination arrangement which comprises two light sources and two optical deviating systems for deflecting the first and second illumination beam paths, respectively, onto the object from different directions. In order to adapt to different working distances of the objective, the mirrors of one of the deviating systems are partially displaceable in the vertical direction so that their vertical distance from the objective is always kept constant. The other illumination beam path is not adapted, so that the illumination with different working distances has a different brightness and is sometimes not focused. In addition, the system can be produced only by tolerating a comparatively large installation height. Furthermore, the need to coordinate operation of two light sources increases complexity and expense.

DE A 197 28 035 discloses a microscope with observation optics having an objective with a variable working distance and with oblique illumination. The illumination beam path comes from a single light source and is split into two beam sub-paths which are respectively directed laterally from the optical axis of the observation optics onto the object. The illumination beam paths are inclined in the region close to the object as a function of the working distance or the focal length (convergence distance) of the objective, so that the beam axes meet approximately at the focal point of the objective. To this end, various deviating mirrors are provided. The deviating mirrors' inclination is respectively adjusted individually as a function of the working distance since the mirrors have to be rotated by different amounts when there is a change in the working distance. As explained below with reference to FIG. 1, adjustment is needed because stationary deviating mirrors would lead to a countersense angle change in the two sub-beams, so that they no longer meet in the region of the optical axis. In order to adjust the mirror settings, DE A 197 28 035 proposes a coupling device which couples the rotational movements of the mirrors mechanically to the object movement. Owing to the multiplicity of components involved, which need to be adapted, this type of convergence distance adaptation is complex and expensive.

SUMMARY OF THE INVENTION

It is therefore an object of the invention to resolve one or more problems of the prior art and to provide an illumination device with which adaptation to different working distances can be carried out in a straightforward way.

This and other objects may be achieved by one or more embodiments described herein. In one embodiment of the present invention, an illumination device for a microscope has a common light source for at least two illumination beam paths, the optical axes of which are inclined relative to the optical axis of the observation optics of the microscope as a function of the working distance of the objective. An object is illuminated obliquely from two different directions. Light coming from the common light source is split into at least two illumination beam paths. In order to adapt to different working distances, the light is subjected to an angle change (variation of the entry angle) before the light is split or, if after the light is split, then respectively by the same amount in both beam paths. So that this angle change does not lead to a countersense change in the angle of the illumination beam paths in the region near the object, as in the prior art, a deviating element having at least two, and an even number of, reflective surfaces is arranged in one of the illumination beam paths. The position and orientation of these surfaces are constant with respect to the objective. The deviating element induces a change in the angle at which the illumination beam path passing through the deviating element strikes the object in the same sense as the change in the corresponding angle for the other illumination beam path. This other illumination beam path does not pass through the deviating element. Assuming that each vertex present in the illumination beam path can be considered a simple reflection, the effect may be generally formulated as: the illumination beam paths have a different number of reflections on mutually coplanar surfaces, the difference being odd. Here, "mutually coplanar" means that the surfaces are all perpendicular to the same incidence plane, not that the surfaces all lie in the same plane.

Here, "same sense" means that the angle between the first illumination beam path and the observation optics' optical axis becomes greater (with a shorter working distance between the objective and the object plane) when the angle between the second illumination beam path and the optical axis becomes greater, and vice versa.

It is, therefore, possible to obviate complicated mutually coordinated variation of the orientation of different deviating elements in the two beam sub-paths. The deviating element in the above-described exemplary embodiment, and optionally further deviating elements which may be combined within a deviating optic, have reflective surfaces that are stationary. Although the reflective surfaces may be adjustable, their position and orientation after initial adjustment, or during operation, do not depend on the current working distance of the objective (i.e. the distance between the objective and the object plane), and do not have to be adapted to that distance.

The adaptation to different working distances is carried out by varying the illumination angle entering the splitting and deviating optic, in particular before it is split into two sub-beams. To this end, mobile reflective surfaces may be provided outside the splitting and deviating optic. As an alternative, adaptation to different working distances may be achieved by a lens movable transversely to the incident beam, or by another deflecting device.

Preferably, the splitting and deviating optic has in total at least three (or an odd number) of at least partially reflective surfaces. Two of the surfaces are assigned to the deviating element described above. A further surface is additionally used to split the beams or make the spatially separated beams intersect in the object plane, so that they strike the object from two different sides. Both cases will be explained in more detail below with reference to the drawings.

At least one of the reflective surfaces may simultaneously also serve as a beam splitter for separating one of the illumination beam paths. The surface may also be designed to be only partially reflective, so that the illumination light of the beam unaffected by the surface does not have strong intensity variations or any shadowing. For example, the deviating element described above may fulfill a beam splitting function as well.

The reflective surfaces are preferably arranged so that the optical axes of the illumination beam paths intersect approximately in the region of the optical axis of the observation optics. The point of intersection can be displaced by varying just one parameter, namely the angle at which the illumination light enters the splitting and deviating optic, in order to adapt the point of intersection, and therefore optionally also the focal plane of the illumination light, to the working distance of the objective. In this way, in particular, it is possible to produce illumination which is centered (symmetrical) with respect to the optical axis of the observation optics. Preferably, for this purpose, the path length difference in the two beam paths is small. For this reason, it is advantageous for the distance, from that reflective surface which separates the beam paths from one another to that surface which causes the deflection of the longer beam path toward the optical axis of the observation optics (assuming the respective last reflective surfaces in the two beam paths are the same distance from the object plane), to be as small as possible.

As an alternative or in addition, a focusing element may be provided in the longer beam path, or a defocusing element may be provided in the shorter beam path, in order to compensate for different broadening of the light which results from the path length difference. This may involve a lens introduced into the beam path, or one of the reflective surfaces could be shaped concavely or convexly.

The aforementioned deviating element has two at least partially reflective surfaces, which are coplanar (i.e. in each case lying perpendicular to the same incidence plane) and make an angle $\alpha$ of preferably less than 90° with one another. This may involve a mirror system with two mirrors mounted in fixed positions relative to one another. In another preferred embodiment, however, the second deviating element is a pentaprism (pentagonal prism), i.e. an optically transparent cylindrical body with a base surface in the form of an axisymmetric quadrilateral or pentagon, in which the mutual arrangement of the surfaces is rigid, does not need to be adjusted and does not change under external mechanical effects.

In a pentaprism or an equivalent mirror system, an incident light beam is deflected through an angle $\delta = 2\alpha$ independently of the angle of incidence of the light beam onto the reflective surfaces, where $\alpha$ is the angle between the two coplanar surfaces. This applies also for a system with more than two reflective surfaces, where there are an even number of such surfaces. Because the pentaprism or equivalent mirror system deflects incident light by the same angle, regardless of the light's angle of incidence, a change in the incoming light's incidence angle changes the angle at which the light emerges from the pentaprism or mirror system by the same amount. Such a pentaprism, introduced suitably into the beam path, fulfills the aforementioned function of the splitting and deviating optic.

According to a method in accordance with an embodiment of the invention, an object, which lies in the object region of a microscope having observation optics with a variable working distance, is to be illuminated from at least two sides at an angle adapted to the working distance. Light from a common light source is injected into at least two illumination beam paths and directed onto the object from different directions. One of the illumination beam paths is subjected to reflection on at least two (or 2n) at least partially reflective surfaces whose position and orientation are constant with respect to an objective, while the other beam path is not reflected on these two surfaces. The inclination of the optical axes of the illumination beam paths relative to the optical axis of the observation optics is varied in the same sense, and preferably by the same amount, by varying an angle of the illumination light relative to the surfaces before reflection on these surfaces. In general, this is achieved by a different number of reflections on stationary surfaces in the two beam paths, the difference being odd.

BRIEF DESCRIPTION OF THE DRAWINGS

A disclosure of the present invention is set forth in this specification, which makes reference to the accompanying drawings, in which.

Figure 1:
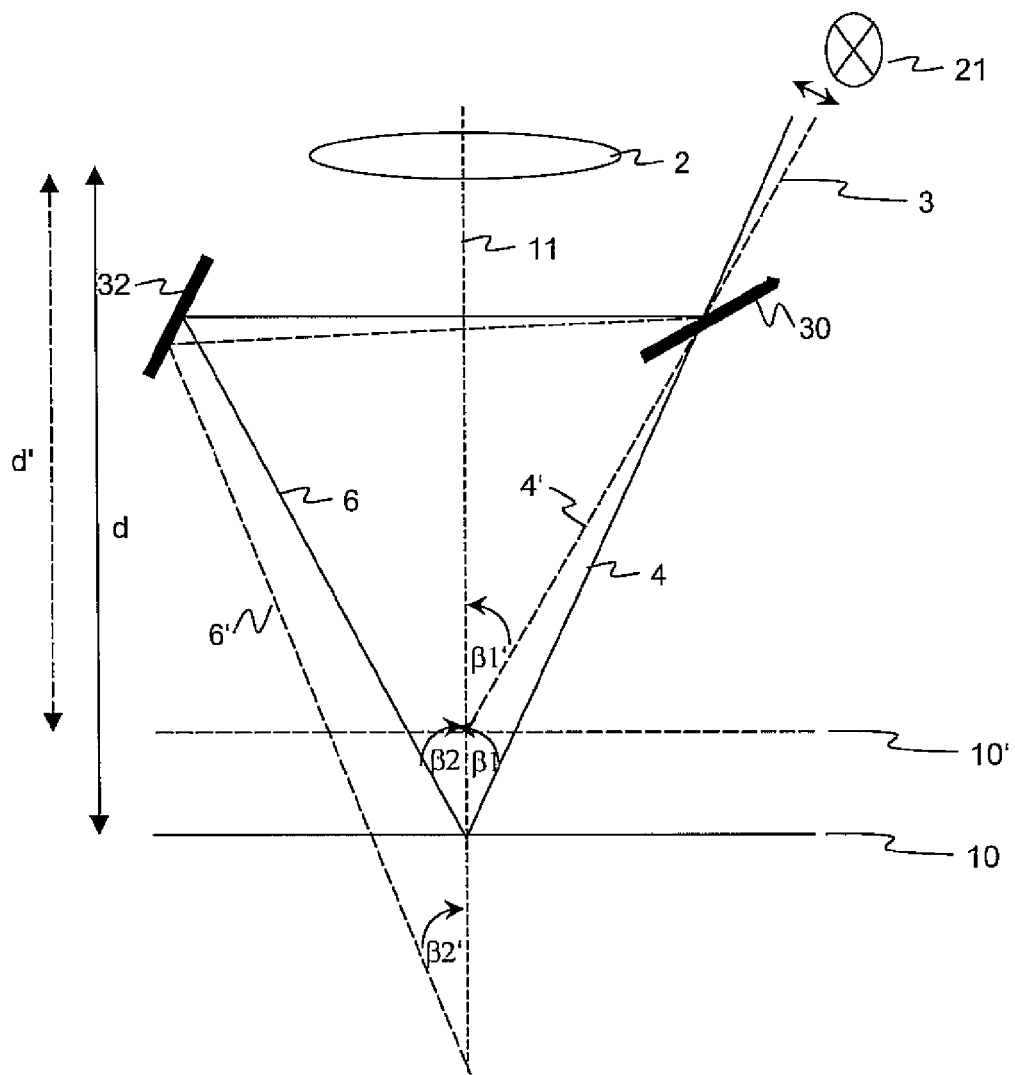
FIG. 1 is a schematic illustration of a prior art illumination device with two mirrors.

Repeat use of reference characters in the present specification and drawings is intended to represent same or analogous features or elements of the invention.

DETAILED DESCRIPTION

Reference will be made in detail to certain embodiments of the invention, one or more examples of which are illustrated in the accompanying drawings.

Referring to FIG. 1, an illumination arrangement for a microscope in the prior art has an objective 2 with a variable working distance d. Light 3 coming from a light source 21 is focused on the one hand as a first illumination beam path 4, at a predetermined angle $\beta 1$ with respect to an optical axis 11 of the objective 2, directly onto an object plane 10. A first deviating element 30 injects light from the primary beam 3 into a second illumination beam path 6, deflecting the light in a direction substantially parallel to object plane 10. A second deviating element 32 subsequently directs the second illumination beam path 6 symmetrically with respect to the first illumination beam path 4 at an angle β2, approximately the same as β1, onto the object plane 10 so that the optical axes of the two illumination beam paths 4, 6 intersect in the region of the optical axis 11 of the observation optics.

In order to adapt to a different, here smaller, working distance d', the angle β1 at which the first illumination beam path 4 is projected onto the object plane 10 is increased, in this example, to β1' (represented by dashes) for beam path 4'. If deviating elements 30, 32 do not change their orientation, second illumination beam path 6 would intersect the optical axis 11 at a plane offset from the modified working distance d'. Angle β2 of the second illumination beam path 6 would be reduced to β2' for beam path 6'—counter to the sense in which angle β1 changed to angle β1'. The distance at which the second illumination beam path 6 intersects the optical axis 11 is increased at 6' rather than being reduced as in the case of illumination beam path 4 at 4'. Symmetrical illumination therefore requires that the orientation of at least the second deviating element is adapted to the modified working distance d'.

Figure 2:
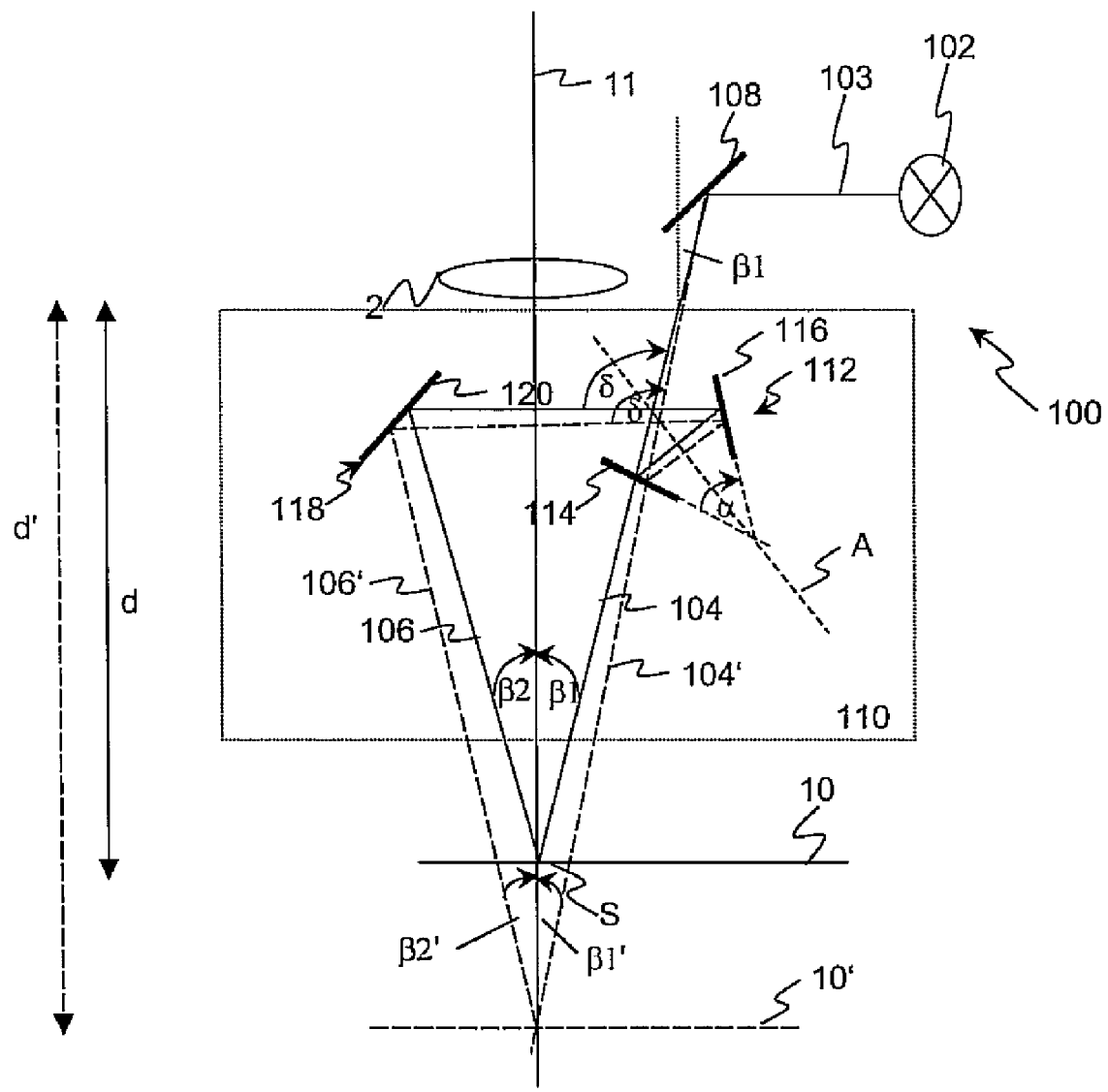
FIG. 2 is a schematic illustration of an illumination device according to an embodiment of the present invention, with three stationary reflective surfaces.

Referring to FIG. 2, an illumination device 100 according to an embodiment of the present invention has a light source 102, the light of which is initially injected into a common beam path 103 which is subsequently split by a deviating optic 110 into two illumination beam paths 104, 106. FIG. 2 illustrates only the optical axes of beam paths 103, 104, 106, represented as solid and dashed lines, for two different working distances d, d', although it should be understood that this is for purposes of illustration only and that the arrangement of FIG. 2 may be configured for multiple different distances other than as shown in FIG. 2. The light is directed obliquely onto object plane 10 from two different directions, so that the optical axes of the illumination beam paths 104, 106 make approximately the same angle β2=β1 with the optical axis 11 of the illumination optics (or objective) 2, and intersect in the object plane 10 in the region of the optical axis 11 of the observation optics. The object (not represented in FIG. 2) is therefore illuminated from two sides, and shadowing by object regions lying above is avoided.

The angle β1, at which the first illumination beam path 104 strikes object plane 10, is proportional to the angle of at which the common beam path 103 enters the splitting and deviating optic 110. Angle β1 can be varied by means of a deflection device 108, for example a mirror or a displaceable lens (see FIGS. 3 and 4). The arrangement shown also makes it possible to vary the angle β2 at which the second illumination beam path 106 arrives at object plane 10, and therefore to displace the point of intersection S of the illumination beam paths 104, 106 along the optical axis 11 of the observation optics 2. The illumination can therefore be adapted to different working distances d, d' by varying just one parameter. In the present case, the angle is reduced from β1 to β1' when the working distance is increased from d to d' (i.e. object plane 10 shifts to object plane 10'), which leads to a change from β2 to β2'=β1' after the light passes through the splitting and deviating optic 110. The correspondingly modified illumination beam paths 104', 106' are represented by dashes.

The splitting of the two illumination beam paths 104, 106 and the adaptation to different working distances is described in more detail below:

Splitting and deviating optic 110 is arranged so that a part of common beam path 103 is not deflected, thereby producing first illumination beam path 104. Beam path 103 and first illumination path 104 extend, for example, at least partially behind the splitting and deviating optic 110 in plan view of the plane of the drawing. The angle (31, at which first illumination beam path 104 strikes object plane 10, is therefore determined only by the setting of the deflection device 108 in relation to the light source 102 and can be adapted to different working distances by varying its setting.

By means of splitting and deviating optic 110, the second illumination beam path 106 is separated from the common beam path 103. A first deviating element 112, through which common beam path 103 passes, has a first reflective surface 114 that is oriented obliquely upwards away from the optical axis 11 of the observation optics 11211. It directs the light onto a second reflective surface 116, which is oriented obliquely downwards towards the optical axis 11 of the observation optics. The two surfaces 114, 116 are coplanar, i.e. they lie perpendicular to the same plane (of the drawing), and make an angle α with respect to one another. In combination, they deflect the second illumination beam path through an angle δ=2α. The deflection angle δ between the common beam and the second illumination beam path is independent of the angle at which the light strikes the first deviating element 112, i.e. independent of the angle β1, but when angle β1 changes to β1', the beam paths forming the angle δ rotate together by the difference angle β1-β1'. The orientation of the first deviating element 112 is selected so that the second illumination beam path 106 is extracted in a direction essentially parallel to object plane 10. A symmetry axis A of first deviating element 112 is oriented at about 45° with respect to optical axis 11 in this embodiment. Deflection angle δ is somewhat more than 90°, so that the obliquely incident beam 103 is deflected in a direction essentially parallel to the object plane as the second illumination beam path 106. On the other side of the objective 2 in relation to the first deviating element 112 and the optical axis 11, there is a second deviating element 118 with a reflective surface 120. The second illumination beam path 106 is thereby deflected towards the object plane 10.

An angle change from β1 to β1' in common beam path 103 leads to an angle change from β2 to β2' in the same sense in the two illumination beam paths 104, 106. That is, both angles are increased or reduced.

The two illumination beam paths 104, 106 preferably intersect in the region of the optical axis 11. By suitable selection of the position and orientation of reflective surfaces 114, 116 and 120, it is possible for the point of intersection S to lie essentially in the region of the optical axis 11 even when there is a variation in the angle β1. The position and orientations of the reflective surfaces 114, 116, 120 remain constant after initial adjustment, even for different working distances. The adaptation to different working distances is carried out only by varying angle β1 at which the common beam path 103 strikes the splitting and deviating optic 110.

The additional reflective surface, compared with FIG. 1 causes the angle change in the two illumination beam paths 104, 106 to be in the same sense, i.e. β1, β2 in the two beam paths are both increased, or both reduced, when the entry angle varies, whereas in FIG. 1 an increase in the one angle β1 leads to a reduction in the other angle β2. With planar reflection surfaces, the degree to which the angles of the two illumination beam paths 104, 106 with respect to the optical axis 11 (i.e. β1/β2 and β1'/β2') match each other's increases as the two deviating elements 112, 118 are separated from one another by a smaller distance in the direction parallel to the object plane. That is, the difference in length between illuminating paths 104 and 106 induces a difference between angles β1 and β2 and between angles β1' and β2'. The difference in length results from the distance between reflection surfaces 112 and 118, and so reduction of this difference increases the degree to which angles β1 and β2 and β1' and β2' are substantially equal.

First reflective surface 114 may also be semitransparent, so as to still transmit a part of the light in first illumination beam path 104 and prevent total shadowing by the first deviating element 112.

The two sub-beams may be spatially separated before the splitting and deviating optic, in which case both sub-beams are subjected equally to the deflection device 108 after the splitting. Only one parameter, namely the setting of the deflection device, therefore needs to be varied in such an arrangement. The splitting function is upstream of the deflection.

Figure 3:
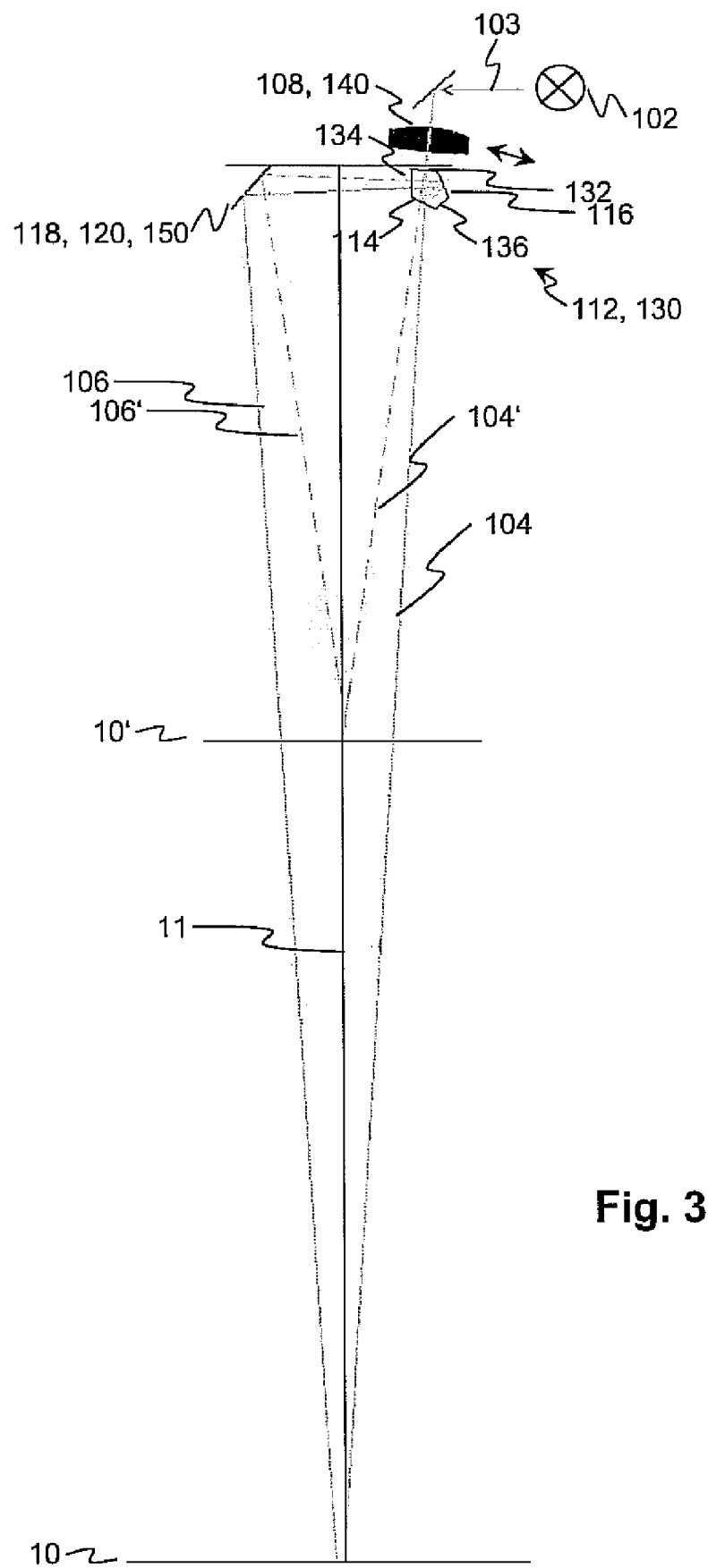
FIG. 3 is a schematic illustration of shows an illumination device according to an embodiment of the present invention, with a pentaprism arranged on an entry side in a deviating arrangement.

FIG. 3 illustrates a further embodiment, in which first deviating element 112 comprises a pentaprism 130. Two side surfaces of the pentaprism 130, which are arranged mirror-symmetrically with respect to axis A, serve as first and second reflective surfaces 114, 116. The entry and exit surfaces 132, 134 are arranged relative to one another and with respect to the common beam path 103 so that the light enters and emerges at an angle of approximately 90° (exactly 90° preferably applies for an average working distance) with respect to the surfaces. The beam is thereby not deflected by refraction at the interfaces, or is deflected only slightly. A fifth side surface 136 of the pentaprism 130 extends, for example, perpendicularly to the axis A but is unimportant for the function of the device. It may therefore also be oriented differently or even not exist at all; in the latter case, the reflective surfaces would adjoin one another directly (i.e. the prism has a quadrilateral instead of pentagonal base shape).

As in FIG. 2, there is a second deviating element 118 with a reflective surface 120 in order to direct the second illumination beam path 106 onto the object plane 10. It is, for example, a mirror 150.

Instead of a rotatable mirror as in FIG. 2, the deflecting optic 108 in the embodiment shown in FIG. 3 is a lens 140 which can be displaced transversely with respect to the optical axis of the common beam path 103 for adaptation of angle β1.

Figure 4:
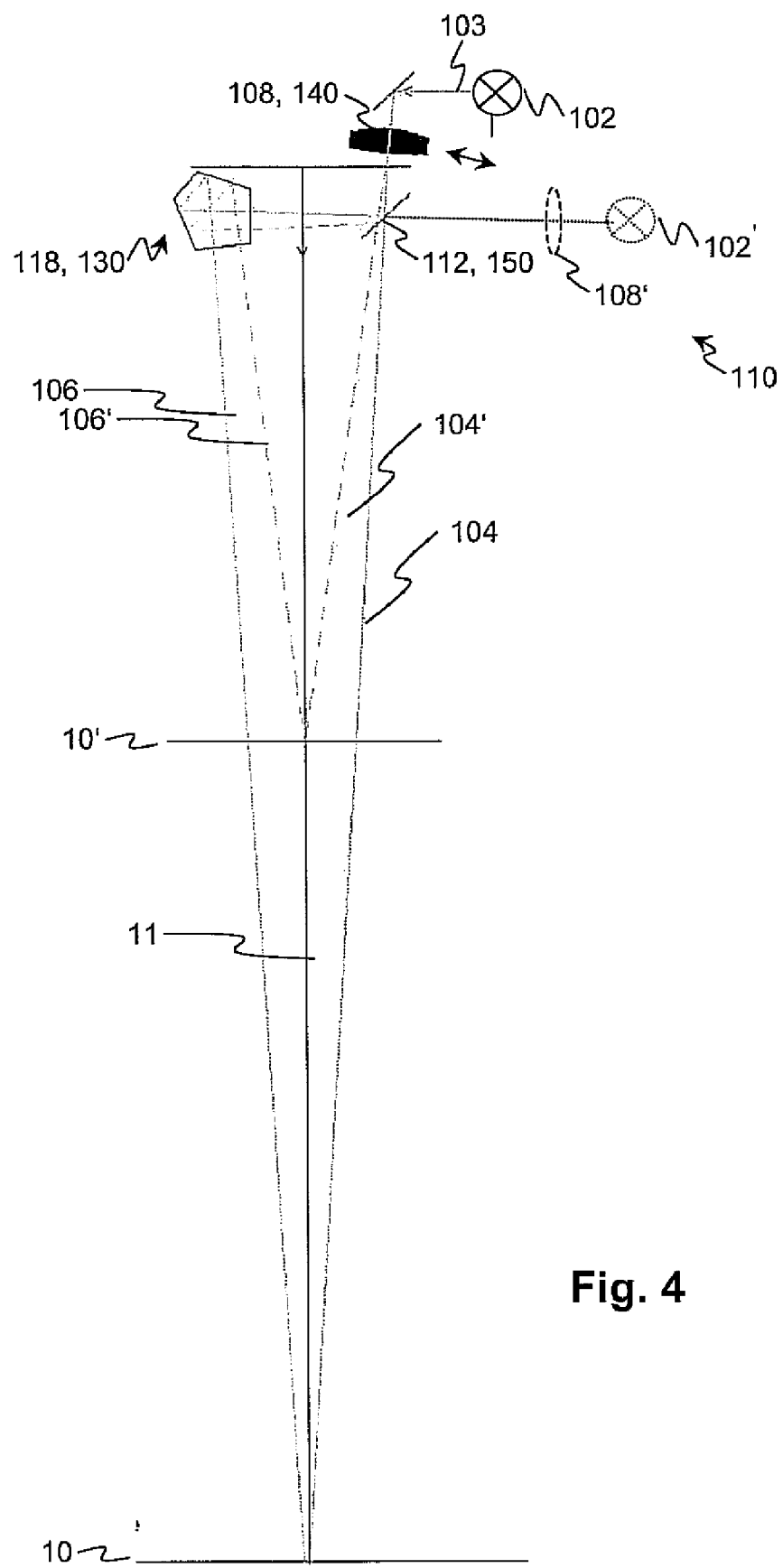
FIG. 4 is a schematic illustration of an illumination device according to an embodiment of the present invention, with a pentaprism arranged on an exit side in the deviating optic.

FIG. 4 illustrates a further embodiment, in which the roles of pentaprism 130 and mirror 150 are interchanged. Mirror 150 functions as first deviating element 112 which deflects the second illumination beam path 106 laterally (i.e. parallel to object plane), whereas the first illumination beam path 104 is guided past the mirror, or through the mirror in the case of a semitransparently configured mirror 150. The pentaprism 130 is arranged on the opposite side of optical axis 11 from the mirror 150. Its entry and exit surfaces 132, 134 are again essentially oriented perpendicularly with respect to the incident and emerging beams. Pentaprism 130 deflects second illumination beam path 106 by a somewhat less than 90° angle downwards. Since the light is already more strongly split here, the base surface of the pentaprism 130 in this variant is larger than in the example of FIG. 3.

FIG. 4 schematically indicates an alternate arrangement (in dashed lines) in which light from a common light source 102' is injected into splitting and deviating optic 110, in this instance laterally (i.e. parallel to the object plane) instead of vertically (i.e. perpendicular to the plant) by a deflection device 108'. First illumination beam path 104 in this embodiment is deflected downwards to object plane 10 by the first deviating element 112, whereas second illumination beam path 106 extends past the first deviating element 112, or through it in the case of a semitransparent mirror 150, in a horizontal direction to second deviating element 118, from which it is deflected downwards.

Figure 5:
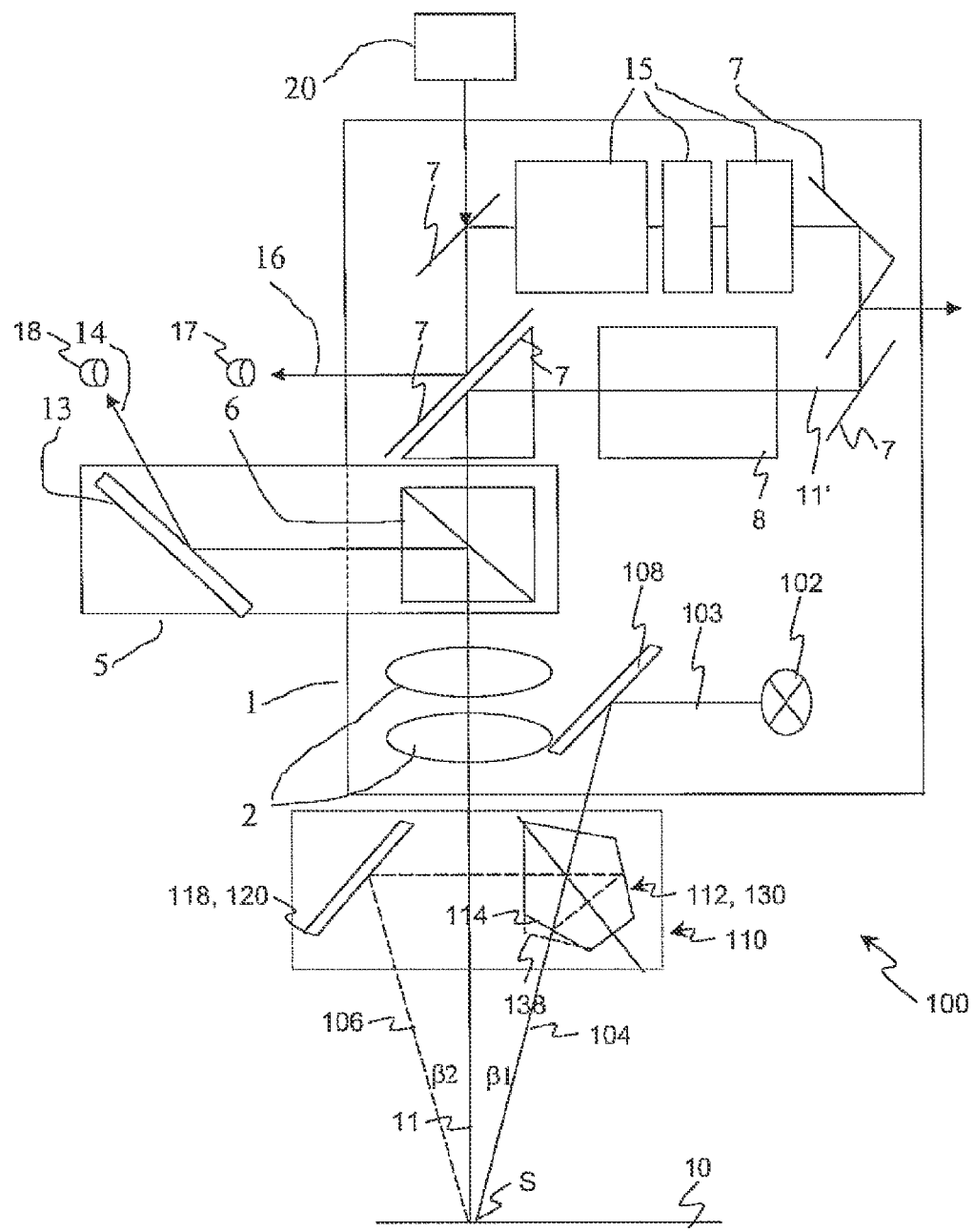
FIG. 5 is a schematic illustration of a microscope according to an embodiment of the present invention.

FIG. 5 illustrates a microscope, having an illumination device 100, according to an embodiment of the present invention. The microscope, which, outside of the illumination device should be well understood, will be described only with respect to the illumination device. The microscope represented is a stereomicroscope with a primary microscope 1 and optionally an assistant microscope 5. It may comprise, for example, an ophthalmological microscope or a microscope used for neurosurgery.

The stereomicroscope has a primary objective 2, a zoom system 8 and at least one binocular tube (not shown) with eyepieces. Optical axis 11 of primary objective 2 extends vertically (in the orientation of FIG. 5) and lies perpendicular to the object plane 10. An observation beam path 16 is deviated repeatedly by deviating elements 7, in each case by 90°, so that the central axis 11' of the zoom system 8 extends horizontally (i.e. parallel to object plane 10). The observation beam path 16 finally reaches the primary observer 17 through a binocular tube (not represented in detail in FIG. 5). Auxiliary optical components 15 are provided in observation beam path 16, for example a data overlay device 20, inverter device, laser shutter device or optical splitter. Owing to the horizontal deviation of observation beam path 16, zoom system 8 and auxiliary components 15 can be installed without thereby increasing the vertical installation height of the stereomicroscope in an ergonomically unfavorable way.

Optionally, between primary objective 2 and first deviating element 7, a further beam splitter 6 is provided which divides primary observation beam path 16 into two beam sub-paths 16, 14 along the optical axis 11 of primary objective 2. A first transmitted beam sub-path 16 corresponds to the beam path already discussed, which extends along the optical axis 11' of the zoom system 8 after deviation. The further beam sub-path 14 is reflected out of the primary observation beam path as an assistant observation beam path and guided through a further deviating element 13 into an assistant binocular tube (not shown), and from there into the eye of the second observer 18. The assistant microscope 5 may, for example, be separable from the primary microscope 1 at a mechanical separation position represented by dashes.

Illumination device 100 comprises a light source 102, which in the present example is arranged laterally from primary objective 2 inside the microscope housing. The light is guided laterally beside the primary objective 2 in common beam path 103 while being deviated downwards by deflection optic 108. Deflection optic 108 is adjustable in order to adapt the aforementioned angle β1 to the working distance. In the splitting and deviating optic 110, the illumination light is split into two illumination beam paths 104, 106 in the manner explained above. In the illumination beam path 103, there may furthermore be illumination optics (not represented in detail FIG. 5).

Splitting and deviating optic 110, with the two deviating elements 112, 118, in this example in the form of a pentaprism 130 and a mirror 150, is preferably located below (with respect to axis 11 between the objective and the object plane) objective 2 so that elements 112 and 118 are on different sides of axis 11. This has the advantage that illumination arrangement 100, or splitting and deviating optic 110, can be configured as an additional component with which a microscope may, for example, be retrofitted or equipped only when needed. Arrangement on the other side of the objective 2 from the object is, however, also possible, in which case the splitting and deviating optic 110 may be integrated into the microscope body.

First reflective surface 114 of pentaprism 130 is preferably only partially reflective, so that a part of the light is transmitted. In order to prevent refraction on this surface, prism 130 has a wedge 138 made of the same material as the pentaprism, which directly adjoins the first reflective surface 114. Wedge 138 is configured so that light passing through the first reflective surface 114 leaves the wedge 138 at an angle of approximately 90° with respect to the wedge surface and is therefore not subjected to refraction at the interface with the air.

A shutter or the like may be arranged in one of the illumination beam paths, in order to use only one or both of the illumination beam paths as required. For example, prism 130 may be configured so that it can be displaced perpendicularly to the plane of the drawing. When it is inserted into the beam path 103, the second illumination beam path 106 is extracted, whereas otherwise all the light reaches object plane 10 through first illumination beam path 104.

A control unit (not shown in FIG. 5) is used to adapt the setting of deflection optic 108 to the current working distance of the objective.

While one or more embodiments of the present invention have been described above, it should be understood that any and all equivalent realizations of the present invention are included within the scope and spirit thereof. Thus, the embodiments presented herein are provided by way of example only.

What is claimed is:

1. An illumination device for a microscope having observation optics having an objective with a variable working distance between the objective and an object plane and having an optical axis comprising:
   a light source that emits light that selectively follows multiple light paths; and
   at least one deviating optic having at least two at least partially reflective surfaces,
   wherein, for each of the multiple light paths, the at least one deviating optic splits the light into at least two beam paths having optical axes that intersect the object plane and that define respective angles with respect to the optical axis of the observation optics,
   wherein a change from one of the multiple light paths to another changes the respective angles and the working distance,
   wherein the at least two at least partially reflective surfaces are in the same position and orientation with respect to the objective at multiple working distances, and
   wherein at least one of the beam paths reflects at each of the at least two at least partially reflective surfaces.

2. The illumination device according to claim 1, wherein the position and orientation of the at least partially reflective surfaces are selected so that the respective angles vary in the same direction when the light path-changes from the one of the multiple light paths to the another of the multiple light paths.

3. The illumination device according to claim 1, wherein the at least one deviating optic has a first deviating element having at least two said at least partially reflective surfaces and a second deviating element with at least one said at least partially reflective surface.

4. The illumination device according to claim 3, wherein a first said beam path passes through the at least one deviating optic substantially without deviation at a first said respective angle, and a second said beam path extends at a second said respective angle after reflection on at least three of the at least partially reflective surfaces, wherein the first respective angle and the second respective angle are substantially the same.

5. The illumination device according to claim 3, wherein a first said beam path is reflected on a first said at least partially reflective surface and subsequently extends at a first said respective angle, and a second said beam path is reflected on at least two other said at least partially reflective surfaces so that it extends at a second said respective angle, wherein the first respective angle and the second respective angle are substantially the same.

6. The illumination device according to claim 1, wherein the at least one deviating optic comprises a first deviating element which has at least a first and a second said at least partially reflective surface in a fixed mutual spatial arrangement with respect to each other.

7. The illumination device as in claim 6, wherein the first deviating element is a pentaprism.

8. The illumination device according to claim 6, wherein the first and second at least partially reflective surfaces make an angle of less than 90° between one another.

9. The illumination device according to claim 6, wherein an angle bisector of the first and second said at least partially reflective surfaces is arranged at an angle of approximately 45° with respect to the optical axis of the observation optics.

10. The illumination device according to claim 6, wherein the at least one deviating optic has a second deviating element with a further reflective surface, the first and second deviating elements being arranged on respective opposite sides of the optical axis of the observation optics.

11. The illumination device according to claim 10, wherein the first and second deviating elements are arranged at substantially the same position between the objective and the object plane.

12. The illumination device according to claim 10, wherein a first said beam path from the light source extends through or past the first deviating element to the object plane without reaching the second deviating element, and a second said beam path from the light source reflects from the first deviating element to the second deviating element before reaching the object plane.

13. The illumination device according to claim 12, wherein the first reflective surface of the first deviating element is semitransparent.

14. The illumination device according to claim 13, wherein the first deviating element is a pentaprism, and the semitransparent first reflective surface is adjoined by a wedge which has the same refractive index as the pentaprism and is configured so that light passing through the first reflective surface leaves the wedge at an angle of approximately 90° with respect to a surface of the wedge.

15. The illumination device according to claim 1, comprising at least one deflecting optic in a light path between the light source and the at least one deviating optic so that the deflecting optic directs light from the light source to the deviating optic, wherein the deflecting optic is adjustable to shift the light between the one of the multiple light paths and the another light path.

16. The illumination device according to claim 15, wherein the deflecting optic comprises a displaceable lens.

17. The illumination device of claim 15, wherein the deflecting optic comprises a rotatable mirror.

18. A method for illuminating an object which is located in an object region of a microscope having observation optics including an objective with a variable working distance between the objective and an object plane and having an optical axis, comprising:
   providing a light source that emits light that selectively follows multiple light paths;
   splitting the light into at least two beam paths having optical axes; and
   directing the at least two beam paths to the object plane so that the at least two beam paths intersect the object plane and define respective angles with respect to the optical axis of the observation optics, wherein a change from one of the multiple light paths to another changes the respective angles and the working distance; and providing a deviating optic having at least two at least partially reflective surfaces, wherein at least one of the beam paths reflects at each of the at least two at least partially reflective surfaces and wherein the at least two at least partially reflective surfaces are in the same position and orientation with respect to the objective at multiple working distances.

19. An illumination device for a microscope having observation optics including an objective with a variable working distance between the objective and an object plane and having an optical axis, comprising:

a light source that emits light that follows a light path;
at least one deviating optic having at least two at least partially reflective surfaces; and
at least one deflecting optic in the light path between the light source and the at least one deviating optic so that the at least one deflecting optic directs light from the light source to the at least one deviating optic so that the at least one deviating optic splits the light from the light source into at least two beam paths having optical axes that intersect the object plane and that define respective angles with respect to the optical axis of the observation optics,
wherein the at least one deflecting optic is adjustable with respect to the light source to thereby shift the light path and change the respective angles and the working distance,
wherein the at least two at least partially reflective surfaces are in the same position and orientation with respect to the objective at multiple working distances, and
wherein at least one of the beam paths reflects at each of the at least two at least partially reflective surfaces.

20. A microscope, comprising:

observation optics having an objective with a variable working distance between the objective and an object plane and having an optical axis;
a light source that emits light that selectively follows multiple light paths; and
at least one deviating optic having at least two at least partially reflective surfaces,
wherein, for each of the multiple light paths, the at least one deviating optic splits the light into at least two beam paths having optical axes that intersect the object plane and that define respective angles with respect to the optical axis of the observation optics,
wherein a change from one of the multiple light paths to another changes the respective angles and the working distance,
wherein the at least two at least partially reflective surfaces are in the same position and orientation with respect to the objective at multiple working distances, and
wherein at least one of the beam paths reflects at each of the at least two at least partially reflective surfaces.

21. The microscope according to claim 20, wherein the position and orientation of the at least partially reflective surfaces are selected so that the respective angles vary in the same direction when the light changes from the one of the multiple light paths to another of the multiple light paths.

22. The microscope according to claim 20, wherein the at least one deviating optic has a first deviating element having at least two said at least partially reflective surfaces and a second deviating element with at least one said at least partially reflective surface.

23. The microscope according to claim 22, wherein a first said beam path passes through the at least one deviating optic substantially without deviation at a first said respective angle, and a second said beam path extends at a second said respective angle after reflection on at least three of the at least partially reflective surfaces, wherein the first respective angle and the second respective angle are substantially the same.

24. The microscope according to claim 22, wherein a first said beam path is reflected on a first said at least partially reflective surface and subsequently extends at a first said respective angle, and a second said beam path is reflected on at least two other said at least partially reflective surfaces so that it extends at a second said respective angle, wherein the first respective angle and the second respective angle are substantially the same.

25. The microscope according to claim 20, wherein the at least one deviating optic comprises a first deviating element which has at least a first and a second said at least partially reflective surface in a fixed mutual spatial arrangement with respect to each other.

26. The microscope as in claim 25, wherein the first deviating element is a pentaprism.

27. The microscope according to claim 25, wherein the first and second at least partially reflective surfaces make an angle of less than 90° between one another.

28. The microscope according to claim 25, wherein the at least one deviating optic has a second deviating element with a further reflective surface, the first and second deviating elements being arranged on respective opposite sides of the optical axis of the observation optics.

29. The microscope according to claim 28, wherein the first and second deviating elements are arranged at substantially the same position between the objective and the object plane.

30. The microscope according to claim 28, wherein a first said beam path from the light source extends through or past the first deviating element to the object plane without reaching the second deviating element, and a second said beam path from the light source reflects from the first deviating element to the second deviating element before reaching the object plane.

31. The microscope according to claim 30, wherein the first at least partially reflective surface of the first deviating element is semitransparent.

32. The microscope according to claim 31, wherein the first deviating element is a pentaprism, and the semitransparent first at least partially reflective surface is adjoined by a wedge which has the same refractive index as the pentaprism and is configured so that light passing through the first at least partially reflective surface leaves the wedge at an angle of approximately 90° with respect to a surface of the wedge.

33. The microscope according to claim 20, comprising at least one deflecting optic in a light path between the light source and the at least one deviating optic so that the deflecting optic directs light from the light source to the at least one deviating optic, wherein the deflecting optic is adjustable to shift the light between the one of the multiple light paths and the another light path.

* * * * *